United States Patent
Khawaled et al.

(10) Patent No.: US 7,775,795 B2
(45) Date of Patent: Aug. 17, 2010

(54) ELECTROCHEMICALLY TREATING TEETH

(75) Inventors: Kamal Khawaled, Shfaram (IL); Maher Jubeh, Jerusalem (IL)

(73) Assignee: Fluorinex Active Ltd., Nazareth (IL)

( * ) Notice: Subject to any disclaimer, the term of this patent is extended or adjusted under 35 U.S.C. 154(b) by 168 days.

(21) Appl. No.: 11/476,787

(22) Filed: Jun. 29, 2006

(65) Prior Publication Data

US 2008/0003540 A1 Jan. 3, 2008

Related U.S. Application Data

(63) Continuation-in-part of application No. PCT/IL2004/001174, filed on Dec. 29, 2004.

(60) Provisional application No. 60/532,570, filed on Dec. 29, 2003.

(51) Int. Cl.
*A61C 3/00* (2006.01)
(52) U.S. Cl. .................................. 433/32; 433/214
(58) Field of Classification Search ......... 433/214–215, 433/80, 32, 37; 128/861–862, 848, 859, 128/860, 724, 733, 774, 777
See application file for complete search history.

(56) References Cited

U.S. PATENT DOCUMENTS

| | | | | |
|---|---|---|---|---|
| 3,380,446 A | * | 4/1968 | Martin | 601/2 |
| 3,527,219 A | | 9/1970 | Greenberg | |
| 5,265,624 A | * | 11/1993 | Bowman | 128/848 |
| 5,490,520 A | * | 2/1996 | Schaefer et al. | 128/848 |
| 5,520,539 A | * | 5/1996 | Divjak | 433/37 |
| 5,562,449 A | | 10/1996 | Jacobs et al. | |
| 5,766,011 A | * | 6/1998 | Sibner | 433/215 |
| 5,863,202 A | | 1/1999 | Fontenot et al. | |
| 6,280,196 B1 | | 8/2001 | Berghash | |
| 6,350,123 B1 | * | 2/2002 | Rizoiu et al. | 433/80 |
| 6,457,973 B1 | * | 10/2002 | Fetz et al. | 433/37 |
| 2003/0069626 A1 | * | 4/2003 | Lattner et al. | 607/134 |

OTHER PUBLICATIONS

International Search Report published Nov. 24, 2005 for PCT/IL04/01174 filed Dec. 29, 2004.
Written Opinion of the International Searching Authority published Jun. 29, 2006 for PCT/IL04/01174 filed Dec. 29, 2004.
International Preliminary Report on Patentability published Jul. 3, 2006 for PCT/IL04/01174 filed Dec. 29, 2004.

* cited by examiner

*Primary Examiner*—Cris L Rodriguez
*Assistant Examiner*—Yogesh Patel
(74) *Attorney, Agent, or Firm*—Martin Fleit; Paul D. Bianco; Fleit Gibbons Gutman Bongini & Bianco PL

(57) ABSTRACT

Electrochemical method for treating teeth: applying metal salt solution to teeth, applying ionizable substance to the teeth, and applying current flow to the teeth so as to ionize the ionizable substance. Electrochemical device for dental treatment: applicator for applying a substance to teeth, having a first end and a second end, a first electrode attached to first end of applicator, second electrode attached to second end of applicator, wherein first electrode and second electrode are configured for current flow through applicator, and an ionizable substance for placement within applicator, wherein ionizable substance is configured for ionization upon application of current flow through the substance. Electrochemical teeth whitening method: applying metal salt solution to teeth, applying an oxidizing agent to teeth exposed to metal salt solution, and applying current flow to the teeth so as to activate and reduce the oxidizing agent for effecting whitening of the teeth.

32 Claims, 8 Drawing Sheets

A-A

A-A

ELECTROCHEMICALLY TREATING TEETH

RELATED APPLICATIONS

This application is a continuation-in-part of PCT Patent Application No. PCT/IL2004/001174 having International Filing Date of Dec. 29, 2004, which claims the benefit of U.S. Provisional Patent Application No. 60/532,570 filed on Dec. 29, 2003. The contents of the above Applications are all incorporated herein by reference.

FIELD AND BACKGROUND OF THE INVENTION

The present invention relates to electrochemically treating teeth, and more particularly, to a method and device for electrochemically treating teeth, especially applicable for fluorinating teeth or for whitening teeth.

Dental Caries (Tooth Decay)

Dental caries, or tooth decay, is the progressive loss of tooth mineral, followed by bacterial invasion into the demineralized tooth. Dental caries is a relatively complex disease. There is abundant evidence that the initiation of caries requires a relatively high proportion of *mutans* streptococci within dental plaque. These bacteria adhere well to the tooth surface, produce higher amounts of acid from sugars than other bacterial types, can survive better than other bacteria in an acid environment, and produce extra-cellular polysaccharides from sucrose. When the proportion of *s. mutans* in plaque is high (in the range of 2-10%), a patient is at high risk for caries. When the proportion is low (less than 0.1%), the patient is at low risk. Two other types of bacteria are also associated with the progression of caries through dentin. These are several species of *lactobacillus*, and *actinomyces viscosus*. These bacteria are highly acidogenic and survive well in acid conditions.

Moreover, diet greatly influences dental caries. Dietary sucrose changes both the thickness and the chemical nature of plaque. Mutans *streptococci* and some other plaque bacteria use the monosaccharide components (glucose and fructose) and the energy of the disaccharide bond of sucrose to assemble extra-cellular polysaccharides. A diet with a high proportion of sucrose therefore increases caries risk.

Fluorinating Teeth

In the context of the field and art of the present invention, 'fluorinating teeth' generally refers to application of any number of chemical or/and physical processes, procedures, or treatments, performed singly or in combination, which results in introducing fluorine, via one or more chemical forms of elemental fluorine, to teeth, or causing teeth to combine, via chemical or/and physical interaction or/and reaction, with fluorine.

The mineral of enamel, cementum and dentin is a highly-substituted calcium phosphate salt called apatite. The apatite of newly-formed teeth is rich in carbonate, has relatively little fluoride and is relatively soluble. Cycles of partial demineralization and then remineralization in a fluoride-rich environment creates apatite with less carbonate and more fluoride, and is less soluble. A main objective of fluorinating teeth is to produce fluoride-rich, low carbonate apatite, which can exhibit as low as one-tenth the solubility of apatite low in fluoride and high in carbonate, a phenomenon which prevents, or at least inhibits, onset and progression of dental caries (tooth decay). Fluorinating teeth via topical fluoride also inhibits acid production by plaque bacteria, where such acid contributes to the formation of dental caries. Fluorinating teeth by consuming fluoridated substances, such as those made by adding fluoride to food and drinks, dentifrices, oral rinses, oral gels, and oral filling materials, can therefore all reduce the solubility of teeth, helping to reduce the occurrence of dental caries. This effect is very beneficial, but the amounts of fluoride that can be added to the diet or used topically are limited by safety considerations. High levels of dietary fluoride can cause mottling of tooth enamel during tooth formation, while swallowing high levels can cause symptoms of poisoning.

Attempts at reducing the concentration of fluoride and/or the amount of time of exposure to fluoride, for fluorinating teeth, have been made. For example, some prior art techniques (methods, devices) involve use of an electrical current to stimulate ion exchange, wherein fluoride ions can be incorporated into the teeth (i.e., fluorination), thereby enhancing resistance to caries formation. However, such prior art techniques are typically based on using an electrical circuit which runs through a non-intra-oral cavity body part of an individual. Such techniques can be classified as iontophoretic or electromotive drug administration (EMDA) types of techniques, i.e., techniques based on non-invasively propelling or introducing pre-determined concentrations or dosages of a charged substance, normally medication or bioactive agent (e.g., fluoride ions), through the skin (i.e., transdermally), into underlying tissue, by repulsive electromotive force using a small electrical charge applied to an iontophoretic chamber or vessel containing a similarly charged active agent and its vehicle. The iontophoretic nature of such techniques tends to result in insufficient fluoride uptake, largely due to electrochemical polarization that occurs in the body due to the presence of potassium in the blood and nerves, which causes a high resistance to fluoride ion flow, thus hampering fluoride uptake.

In spite of the relatively well developed state in the art of using fluoride in techniques for fluorinating teeth, there remains on on-going need for improving existing techniques, and identifying new techniques, which improve control of applying, delivering, or dispensing, of fluoride to teeth, and involve minimal exposure of non-intra-oral cavity body parts to fluoride.

Whitening Teeth (Teeth Whitening)

In the context of the field and art of the present invention, 'whitening teeth' (or teeth whitening) generally refers to application of any number of chemical or/and physical (mechanical) processes, procedures, or treatments, performed singly or in combination, which results in returning, or/and providing, white color to teeth.

Hydrogen peroxide, and other relatively strong oxidizing agents, at appropriate concentrations and conditions of oral application, are most commonly used for whitening teeth. Teeth are exposed to such strong oxidizing agents, whereby the oxidizing agents oxidize, and possibly also chemically degrade, substances which discolor teeth. However, applications of techniques for whitening teeth based on use of oxidizing agents, are typically accompanied by inadvertent or unpreventable, and undesirable, exposure of non-tooth intra-oral cavity components, e.g., gum and tissue exterior surfaces, to the oxidizing agents. In spite of the relatively well developed state in the art of using oxidizing agents in techniques for whitening teeth, there remains on on-going need for improving existing techniques, and identifying new techniques, which improve control of applying, delivering, or dispensing, of teeth whitening oxidizing agents to teeth, and involve minimal exposure of non-tooth intra-oral cavity components, e.g., gum and tissue exterior surfaces, to oxidizing agents.

There is thus a widely recognized need for, and it would be highly advantageous to have, a method and device for electrochemically treating teeth, especially applicable for fluorinating teeth or for whitening teeth, which are devoid of the above described limitations. Moreover, there is need for such an invention which is relatively simple and inexpensive to manufacture, which is relatively simple, safe, and inexpensive, to implement either by a dental health provider in a dental health office, or by oneself outside of a dental health office, and which is commercially applicable.

SUMMARY OF THE INVENTION

The present invention relates to electrochemically treating teeth, and more particularly, to a method and device for electrochemically treating teeth, especially applicable for fluorinating teeth or for whitening teeth. For fluorinating teeth, implementation of the present invention provides excellent control of (electrochemically) applying, delivering, or dispensing, of fluoride to teeth, and involves minimal exposure of non-intra-oral cavity body parts to fluoride. For whitening teeth, implementation of the present invention provides excellent control of (electrochemically) applying, delivering, or dispensing, of teeth whitening oxidizing agents to teeth, and involves minimal exposure of non-tooth intra-oral cavity components, e.g., gum and tissue exterior surfaces, to oxidizing agents. The present invention is relatively simple and inexpensive to manufacture, and is relatively simple, safe, and inexpensive, to implement either by a dental health provider in a dental health office, or by oneself outside of a dental health office, and is commercially applicable.

According to one aspect of the present invention, there is provided a method for treating a tooth. The method includes applying a metal salt solution to a tooth, applying an ionizable substance to the tooth, and applying a current flow to the tooth so as to ionize the ionizable substance.

According to another aspect of the present invention, there is provided a device for pre-treatment of teeth. The device includes a tray having an upper portion and a lower portion, a sealing lip on the upper portion for enabling close contact between the device and the gums (for sealing), and an absorbent material in the lower portion for receiving an activation solution.

According to another aspect of the present invention, there is provided a device for dental treatment. The device includes an applicator for applying a substance to a tooth, the applicator having a first end and a second end, a first electrode attached to a first end of the applicator, a second electrode attached to the second end of the applicator, wherein the first electrode and the second electrode are configured to produce a current flow through the applicator, and an ionizable substance for placement within the applicator, wherein the ionizable substance is configured to undergo ionization upon application of the current flow through the substance.

According to further features in preferred embodiments of the invention described below, the activation is achieved by using a metal salt solution such as silver nitrate, palladium hydroxide, palladium chloride, copper chloride, or any other suitable solution. In a preferred embodiment, the step of applying a metal salt solution precedes the other steps. In one embodiment, the tooth is rinsed with distilled water after the metal salt solution is applied. In a preferred embodiment, the applying of the metal salt solution is done using a pre-treatment tray which is designed to prevent leakage of the metal salt solution into the mouth. The ionizable substance includes a fluoride compound, preferably sodium fluoride, lithium fluoride, amino fluoride, tin fluoride, or any other suitable fluoride ion donor. The current flow is applied at a voltage within a range of 0.001 volt-12 volts, and more preferably, within a range of 3 volts to 9 volts. The current may be applied via power supply, rechargeable battery, or a disposable battery embedded within the dental treatment device.

According to further features in preferred embodiments of the invention, the pre-treatment device further includes an adhesive material placed on the sealing lip for further enabling of close contact between the device and the gums. Alternatively, or in addition to the adhesive material, the tray itself may be comprised of heatable plastic material which can be formed onto the teeth and gums during application. The activation solution is a metal salt solution, preferably one of the following: silver nitrate, palladium hydroxide, palladium chloride, copper chloride, or titanium chloride, but may include any suitable metal salt solution.

According to further features in preferred embodiments of the invention described below, the applicator is a dental tray or a toothbrush. The ionizable substance is a fluoride compound, such as sodium fluoride, lithium fluoride, tin fluoride, amino fluoride, or a combination of fluoride compounds. In the case of a dental tray, the first end is a back curved wall and the first electrode is an anode, which is preferably a flat metal strip. Spacers made of biocompatible plastic are placed on the anode to separate the anode from the tooth. The second end is a front wall and the second electrode is a cathode having a spring mechanism. Preferably, three cathodes are present, each of which is configured to contact a separate tooth, wherein the contact area is minimized. The dental tray may include a sealing lip. In one embodiment, the device includes a power supply, which can be an external electrical power source, a rechargeable battery, or a disposable battery embedded in the device.

According to another aspect of the present invention, there is provided a method for electrochemically whitening a tooth. The electrochemical tooth whitening method includes applying a metal salt solution to the tooth, applying an oxidizing agent to the tooth exposed to the metal salt solution, and applying a current flow to the tooth so as to activate and reduce the oxidizing agent for effecting the whitening of the tooth.

According to another aspect of the present invention, there is provided a device for electrochemically whitening a tooth. The tooth whitening device includes an applicator for applying a substance to a tooth, the applicator having a first end and a second end, a first electrode attached to a first end of the applicator, a second electrode attached to the second end of the applicator, wherein the first electrode and the second electrode are configured to produce a current flow through the applicator, and an oxidizing agent for placement within the applicator, wherein the oxidizing agent is configured to undergo activation and reduction upon application of the current flow through the oxidizing agent.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
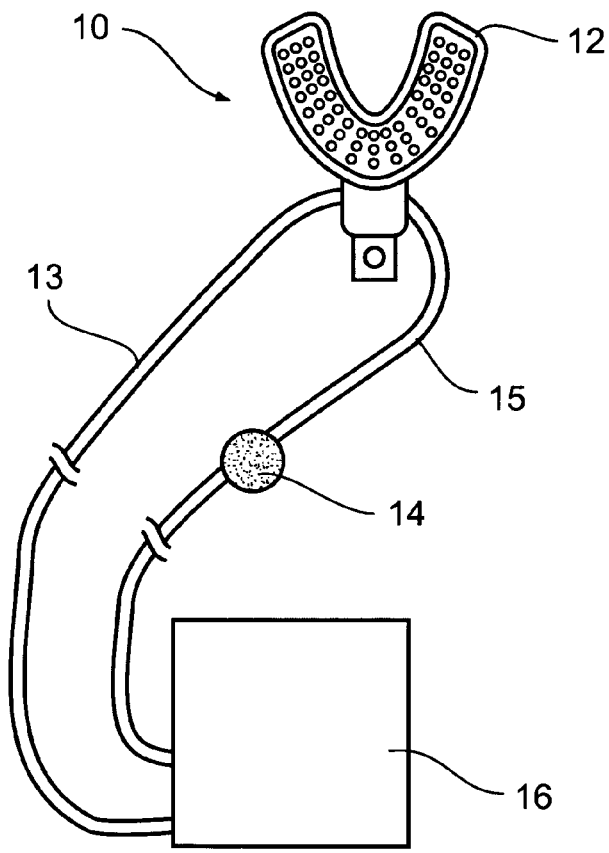
FIG. 1 is a prior art iontophoretic type dental device.

The present invention relates to electrochemically treating teeth, and more particularly, to a method and device for electrochemically treating teeth, especially applicable for fluorinating teeth or for whitening teeth. For fluorinating teeth, implementation of the present invention provides excellent control of (electrochemically) applying, delivering, or dispensing, of fluoride to teeth, and involves minimal exposure of non-intra-oral cavity body parts to fluoride. For whitening teeth, implementation of the present invention provides excellent control of (electrochemically) applying, delivering, or dispensing, of teeth whitening oxidizing agents to teeth, and involves minimal exposure of non-tooth intra-oral cavity components, e.g., gum and tissue exterior surfaces, to oxidizing agents. The present invention is relatively simple and inexpensive to manufacture, and is relatively simple, safe, and inexpensive, to implement either by a dental health provider in a dental health office, or by oneself outside of a dental health office, and is commercially applicable.

The present invention provides for enhanced fluoride treatment of the teeth. Specifically, the present invention can be used to increase the uptake of fluoride and/or decrease the uptake of plaque by application of a preparatory solution followed by application of a treatment fluoride-enriched gel and the application of an electrical current directly to the teeth.

A main aspect of the present invention is provision of a method for treating a tooth, including the following main procedures, and, components and functionalities thereof: applying a metal salt solution to a tooth, applying an ionizable substance to the tooth, and applying a current flow to the tooth so as to ionize the ionizable substance.

Another main aspect of the present invention is provision of a device for pre-treatment of teeth, including the following main components and functionalities thereof: a tray having an upper portion and a lower portion, a sealing lip on the upper portion for enabling close contact between the device and the gums (for sealing), and an absorbent material in the lower portion for receiving an activation solution.

Another main aspect of the present invention is provision of a device for dental treatment, including the following main components and functionalities thereof: an applicator for applying a substance to a tooth, the applicator having a first end and a second end, a first electrode attached to a first end of the applicator, a second electrode attached to the second end of the applicator, wherein the first electrode and the second electrode are configured to produce a current flow through the applicator, and an ionizable substance for placement within the applicator, wherein the ionizable substance is configured to undergo ionization upon application of the current flow through the substance.

Another main aspect of the present invention is provision of a method for electrochemically whitening a tooth, including the following main procedures, and, components and functionalities thereof: applying a metal salt solution to a tooth, applying an oxidizing agent to the tooth, and applying a current flow to the tooth so as to activate and reduce the oxidizing agent for effecting whitening of the tooth.

Another main aspect of the present invention is provision of a device for electrochemically whitening a tooth, including the following main components and functionalities thereof: an applicator for applying a substance to a tooth, the applicator having a first end and a second end, a first electrode attached to a first end of the applicator, a second electrode attached to the second end of the applicator, wherein the first electrode and the second electrode are configured to produce a current flow through the applicator, and an oxidizing agent substance for placement within the applicator, wherein the oxidizing agent substance is configured to undergo activation and reduction upon application of the current flow through the oxidizing agent substance.

The present invention includes several aspects, and special technical features, of novelty and inventiveness over prior art teachings of treating teeth, in general, and, of fluorinating teeth or whitening teeth, in particular.

A main aspect, and special technical feature, of novelty and inventiveness of the present invention is that structure and function, and subsequently, operation, of the (electrochemical) dental treatment device, and implementation of the (electrochemical) dental treatment method, are self-contained and localized with respect to the tooth (teeth) being (electrochemically) treated (i.e., by fluorination or by whitening).

Namely, the electrochemical circuit formed and activated during operation of the (electrochemical) dental treatment device, for fluorinating teeth, or for whitening teeth, does not require, or involve, any non-intra-oral cavity body part, for electrochemically applying, delivering, or dispensing, of fluoride, or teeth whitening oxidizing agents, to the treated tooth (teeth).

For fluorinating teeth, implementation of the present invention provides excellent control of (electrochemically) applying, delivering, or dispensing, of fluoride to teeth, and involves minimal exposure of non-intra-oral cavity body parts to fluoride. For whitening teeth, implementation of the present invention provides excellent control of (electrochemically) applying, delivering, or dispensing, of teeth whitening oxidizing agents to teeth, and involves minimal exposure of non-tooth intra-oral cavity components, e.g., gum and tissue exterior surfaces, to oxidizing agents.

In addition to the preceding aspects of novelty and inventiveness, the present invention is relatively simple and inexpensive to manufacture, and is relatively simple, safe, and inexpensive, to implement either by a dental health provider in a dental health office, or by oneself outside of a dental health office.

It is to be understood that the present invention is not limited in its application to the details of the order or sequence, and number, of procedures, steps, and sub-steps, of operation or implementation of the method, or to the details of type, composition, construction, arrangement, order, and number, of the assemblies, sub-assemblies, mechanisms, structures, components, elements, and configurations, and, peripheral equipment, utilities, accessories, chemical reagents, and materials, of the device, set forth in the following illustrative description, accompanying drawings, and examples, unless otherwise specifically stated herein. Accordingly, the present invention is capable of other embodiments and of being practiced or carried out in various ways. Although procedures, steps, sub-steps, and system units, system sub-units, devices, assemblies, sub-assemblies, mechanisms, structures, components, elements, and configurations, and, peripheral equipment, utilities, accessories, chemical reagents, and materials, which are equivalent or similar to those illustratively described herein can be used for practicing or testing the present invention, suitable procedures, steps, sub-steps, and system units, system sub-units, devices, assemblies, sub-assemblies, mechanisms, structures, components, elements, and configurations, and, peripheral equipment, utilities, accessories, chemical reagents, and materials, are illustratively described and exemplified herein.

It is also to be understood that all technical and scientific words, terms, or/and phrases, used herein throughout the present disclosure have either the identical or similar meaning as commonly understood by one of ordinary skill in the art to which this invention belongs, unless otherwise specifically defined or stated herein. Phraseology, terminology, and, notation, employed herein throughout the present disclosure are for the purpose of description and should not be regarded as limiting. Additionally, as used herein, the term 'about' refers to ±10% of the associated value.

Moreover, all technical and scientific words, terms, or/and phrases, introduced, defined, described, or/and exemplified, in the above Background section, are equally or similarly applicable in the illustrative description of the preferred embodiments, examples, and appended claims, of the present invention.

Procedures, steps, sub-steps, and, equipment and materials, assemblies, sub-assemblies, mechanisms, structures, components, elements, and configurations, and, peripheral equipment, utilities, accessories, chemical reagents, and materials, as well as operation and implementation, of exemplary preferred embodiments, alternative preferred embodiments, specific configurations, and, additional and optional aspects, characteristics, or features, thereof, of electrochemically treating teeth, according to the present invention, are better understood with reference to the following illustrative description and accompanying drawings. Throughout the following illustrative description and accompanying drawings, same reference numbers, refer to same assemblies, sub-assemblies, mechanisms, structures, components, elements, and configurations, and, peripheral equipment, utilities, chemical reagents, accessories, and materials.

In the following illustrative description of the method and device of the present invention, included are main or principal procedures, steps, and sub-steps, and, main or principal assemblies, sub-assemblies, mechanisms, structures, components, elements, and configurations, and, peripheral equipment, utilities, accessories, chemical reagents, and materials, needed for sufficiently understanding proper 'enabling' utilization and implementation of the disclosed invention. Accordingly, description of various possible preliminary, intermediate, minor, or/and optional, procedures, steps, or/and sub-steps, or/and, system units, system sub-units, devices, assemblies, sub-assemblies, mechanisms, structures, components, elements, and configurations, and, peripheral equipment, utilities, accessories, chemical reagents, and materials, of secondary importance with respect to enabling implementation of the invention, which are readily known by one of ordinary skill in the art, or/and which are available in the prior art and technical literature relating to the field of the present invention, are at most only briefly indicated herein.

Figure 2:
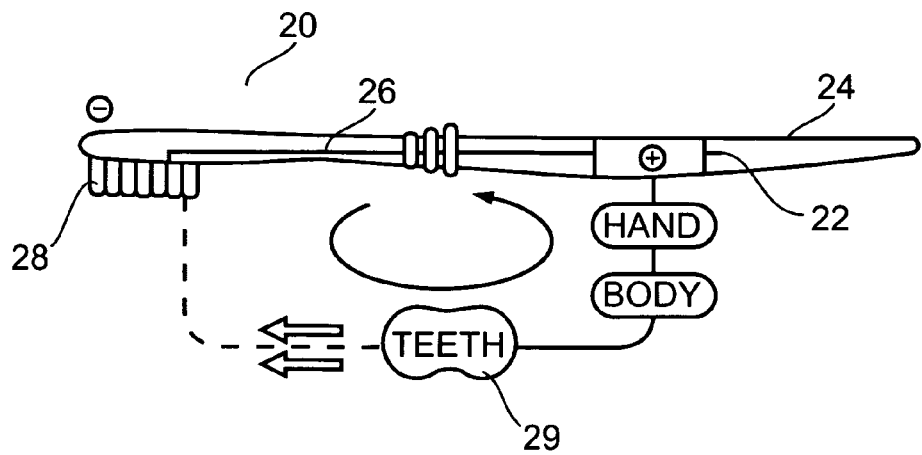
FIG. 2 is a prior art iontophoretic type toothbrush.

For purposes of better understanding the present invention, as illustrated in FIGS. 3-8 of the drawings, reference is first made to the construction and operation of prior art iontophoretic type dental devices, particularly intended to be used for fluorinating teeth, as illustrated in FIGS. 1 and 2.

As shown in FIG. 1, a prior art system 10 for iontophoretic type of uptake of fluoride includes a metallic tray 12, which acts as a first (negative) electrode, connected with a first wire 13 to a power supply 16, and connected with a second wire 15 to a second (positive) electrode 14, which is further connected to power supply 16. Second electrode 14 is designed to be in contact with a location on a body of an individual undergoing the procedure provided herein. An ionizable form of fluoride, such as lithium fluoride, is incorporated in a gel matrix and placed within metallic tray 12. Metallic tray 12 is coated with a non-conducting material, or alternatively, the tray itself comprises non-conducting material, and includes thereon the first electrode. In either case, the tray filled with the fluoride gel is placed in contact with the teeth of the individual. A current is applied via power supply 16, causing ionization of the fluoride, and thereby providing fluoride ions in a form that can be assimilated into the tooth structure. The circuit for ionization to occur is completed through the body of the individual, thus classifying it as an iontophoretic type of device.

It has been shown that in systems such as the one depicted in FIG. 1, in which the circuit runs through the body of the individual, fluoride uptake is insufficient. This result is likely due to electrochemical polarization that occurs in the body due to the presence of potassium in the blood and nerves, which causes a high resistance to fluoride ion flow, thus hampering fluoride uptake.

Reference is now made to FIG. 2, which is an illustration of a prior art ionic toothbrush 20. As shown in FIG. 2, ionic toothbrush 20 has a battery 22 located on a handle 24 of ionic toothbrush 20. A metal rod 26 runs through the body of ionic toothbrush 20 and into the area of bristles 28. When battery 22 is active, bristles 28 take on a negative charge. At the same time, positively charged ions are transferred to the teeth 29 via the conducting pathway through a moist hand holding the positively charged handle 24. Thus, the polarity of the teeth 29 is changed from negative to positive. The now positively charged teeth repel the positively charged plaque ions, which are furthermore attracted to the negatively charged toothbrush bristles 28. Moist finger contact is essential to maximize ionic transfer. Similar to the prior art iontophoretic type dental tray depicted in FIG. 1, the circuit is completed only through the body of the user, resulting in electrochemical depolarization, which decreases the ionization and thus the plaque transfer within the system.

The present invention relates to electrochemically treating teeth, and more particularly, to a method and device for electrochemically treating teeth, especially applicable for fluorinating teeth or for whitening teeth.

Electrochemistry theory, principles, and practices thereof, and, related and associated applications and subjects thereof, are well known and taught about in the prior art, and currently practiced in a wide variety of numerous different fields and areas of technology. For the purpose of establishing the scope, meaning, and field(s) or area(s) of application, of the present invention, herein following are provided selected definitions and exemplary usages of terminology which are relevant to, and used for, disclosing the present invention.

Electrochemistry—Oxidation, Reduction, and Ionization, Reactions

The term 'electrochemistry' is defined as the science that deals with the use of electrical energy to bring about a chemical reaction or with the generation of electrical energy by means of chemical action. Moreover, if a chemical reaction is caused by an external voltage, or if a voltage is caused by a chemical reaction, then, the chemical reaction is an electrochemical reaction.

In general, electrochemistry deals with oxidation, reduction, and ionization, types of chemical reactions. In general, an oxidation reaction is a chemical reaction which is based on the loss of an electron by a chemical species (atom, molecule, radical, or ion). In general, a reduction reaction is a chemical reaction which is based on the gain of an electron by a chemical species (atom, molecule, radical, or ion). A paired or complementary set of an oxidation reaction and a reduction reaction is commonly referred to as a 'redox' reaction. In general, ionization refers to the process of converting a chemical species (atom, molecule, radical) into an ion, and also refers to the state of a chemical species (atom, molecule, radical) being ionized, where an ion is an atom, a group of atoms, or a molecule, having a net (positive or negative) electrical charge. In general, an 'ionizable substance' refers to a substance which either is, or includes, a chemical species (atom, molecule, radical), that can be ionized, such that there is a change in the net electrical charge of the chemical species which is ionized.

In general, an 'oxidizing agent', also known as an oxidizer or as an oxidant, refers to a chemical compound that readily gives up (atomic or/and molecular) oxygen. An oxidizing agent also refers to a substance that gains (receives) electrons in a redox chemical reaction, whereby the oxidizing agent becomes reduced.

Electrochemically Treating Teeth—Fluorinating, Teeth, or Whitening Teeth (Teeth Whitening)

Herein, in the context of the present invention, 'electrochemically treating teeth' generally refers to using electrical energy to bring about, or cause, the occurrence of one or more oxidation, reduction, or/and ionization, type chemical reactions, i.e., electrochemical reactions, which is/are involved in, and result(s) in, treating teeth. Herein, treating teeth particularly refers to fluorinating teeth, or, alternatively, whitening teeth (teeth whitening).

As previously stated hereinabove, in the context of the field and art of the present invention, 'fluorinating teeth' generally refers to application of any number of chemical or/and physical processes, procedures, or treatments, performed singly or in combination, which results in introducing fluorine, via one or more chemical forms of elemental fluorine, to teeth, or causing teeth to combine, via chemical or/and physical interaction or/and reaction, with fluorine.

As previously stated hereinabove, in the context of the field and art of the present invention, 'whitening teeth' (or teeth whitening) generally refers to application of any number of chemical or/and physical (mechanical) processes, procedures, or treatments, performed singly or in combination, which results in returning, or/and providing, white color to teeth.

Figure 3:
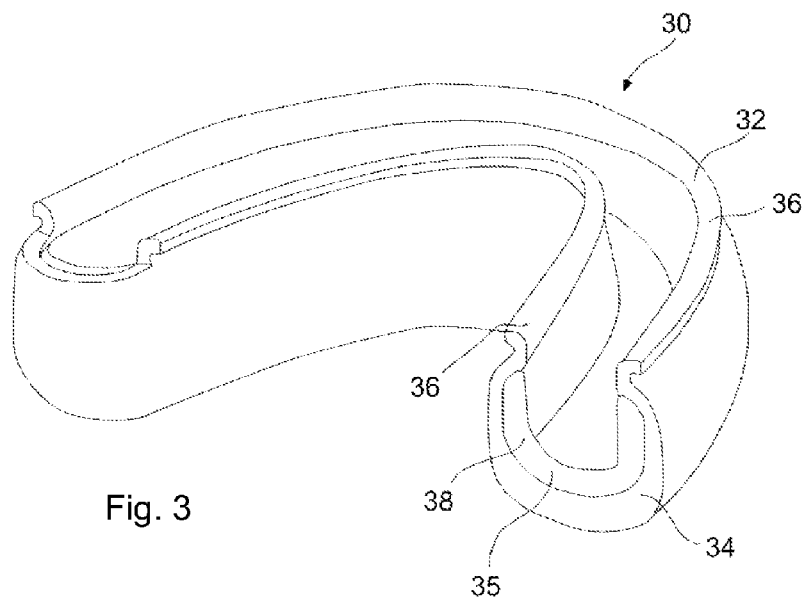
FIG. 3 is an illustration of a pre-treatment tray, in accordance with a preferred embodiment of the present invention.

Reference is now made to FIG. 3, which is an illustration of a pre-treatment tray 30, in accordance with a preferred embodiment of the present invention. Pre-treatment tray 30 is designed to hold an activation solution for immersion of the teeth prior to fluorination treatment with an ionizable substance, such as fluoride solution or gel composition, or, alternatively, prior to whitening treatment using an oxidizing agent, such as hydrogen peroxide. The activation solution will be described in further detail hereinbelow. Pre-treatment tray 30 has an upper portion 32 and a lower portion 34. Upper portion 32 includes a sealing lip 36, which is designed to contact the gums, thus, sealing pre-treatment tray 30 onto the gums and substantially preventing leaking out of activation solution. Lower portion 34 includes a space 35, preferably having an absorbent material 38 therein. In a preferred embodiment, absorbent material 38 is a high density sponge. Absorbent material 38 is designed to absorb the activating solution, and further prevent leakage of the activating solution. In a preferred embodiment, a pre-measured amount of activating solution is introduced directly into absorbent material 38 prior to placing pre-treatment tray 30 on the teeth, so as to ensure that a suitable amount of activating solution is used for full immersion of the teeth without excessive solution being present. In an alternative embodiment of pre-treatment tray 30, space 35 is empty.

In one embodiment of the present invention, pre-treatment tray 30 is comprised of a plastic material which can be heated and formed on the teeth and gums during application. Alternatively, an adhesive material which is biocompatible (such as, for example, beeswax) may be added to sealing lip 36 to further ensure sealing of pre-treatment tray 30 onto the gums.

The activating solution prepares the surface of the teeth to make them receptive to the ionic (electrochemical) changes that are designed to occur during operation of the apparatus or device described herein. The activating solution includes a metal or metallic salt, such as silver nitrate, palladium hydroxide, palladium chloride, copper chloride, or titanium chloride, or any other suitable activator. In a preferred embodiment of the present invention, the activating solution is applied through teeth immersion in the application pre-treatment tray 30 of FIG. 3. In yet another, less preferred embodiment of the present invention, the activating solution is prepared as a rinse, similar to mouthwash. The metal or metal salts provide a preparatory surface on the teeth, wherein the tooth surface adsorbs the material, for example, silver or its ion, thereby, the electric conductivity of the tooth surface for the flowing current is increased (or the electric resistance of the treated tooth surface to the flowing current is decreased). When the present invention is implemented particularly for fluorinating teeth, then, this process facilitates substitution of the hydroxyl group bound to apatite with the fluoride present in the medium. Once the tooth surface is prepared, the metal is rinsed out, and subsequently, a treatment device (either tray or toothbrush) is applied to the teeth, as described below.

Figure 4:
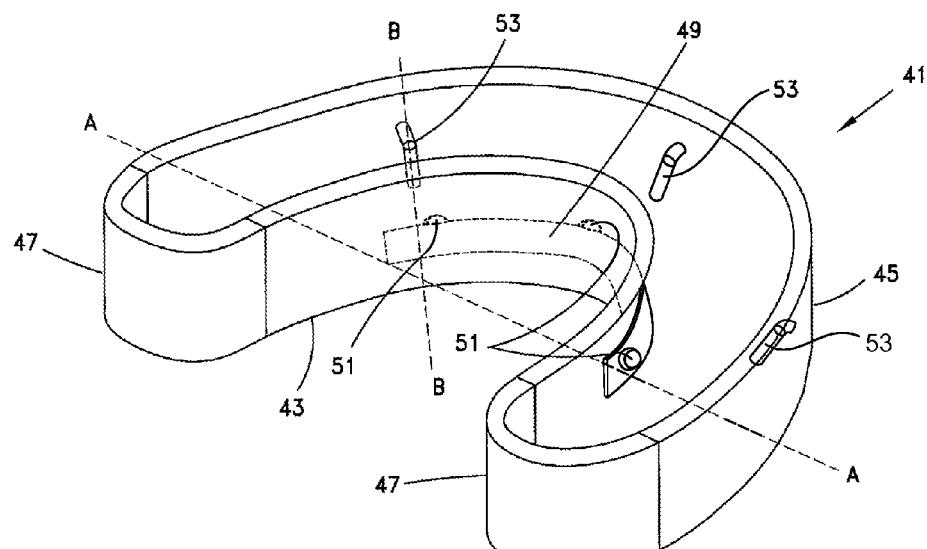
FIG. 4 is an isometric view of a device for electrochemically treating teeth, in accordance with a preferred embodiment of the present invention.

Reference is now made to FIG. 4, which is an isometric view of a device 41, which is usable for electrochemical ion exchange fluoride treatment, i.e., when the present invention is implemented particularly for fluorinating teeth, or, alternatively, which is usable for electrochemical redox reactions involving the oxidizing agent, in teeth whitening treatment, i.e., when the present invention is implemented particularly for whitening teeth, in accordance with a preferred embodiment of the present invention. Device 41 includes a treatment tray designed to hold an ionizable substance, for example, either being, or including, fluoride solution or gel composition, for immersion of teeth therein, i.e., when the present invention is implemented particularly for fluorinating teeth, or, alternatively, is designed to hold an oxidizing agent, for example, either being, or including, a form of hydrogen peroxide, such as a solution form of hydrogen peroxide, for immersion of teeth therein, i.e., when the present invention is implemented particularly for whitening teeth.

Device 41 is of a shape similar to typical dental trays, including a back curved wall 43 and a front curved wall 45 joined together at end sections 47. Back curved wall 43 includes an electrode 49, which is the negative electrode, or the anode. Electrode 49 is comprised of a thin, flexible metal strip attached to an inner portion of back curved wall 43. In a preferred embodiment, electrode 49 is comprised of stainless steel. In alternative embodiments, electrode 49 is comprised of any inert, electricity conducting, material, such as, platinum, gold, or any other suitable electricity conducting metal. Spacers 51 are positioned along electrode 49, and are designed to preclude contact between electrode 49 and teeth positioned within device 41, while providing contact between the ionizable substance, such as fluoride solution or gel composition, or, alternatively, the oxidizing agent, such as hydrogen peroxide solution, within device 41 and electrode 49. Spacers 51 are comprised of insulating materials, such as plastics.

Front curved wall 45 includes contact electrodes 53, which are positive electrodes, or cathodes, and are designed to be placed in direct contact with the front of teeth within device 41. Contact electrodes 53 are attached to front curved wall 45 by a spring-like mechanism, ensuring contact between contact electrodes 53 and the teeth. Preferably, at least three contact electrodes 53 are used, each one designed to contact a different tooth. The contact area between contact electrodes 53 and the teeth is minimized. In a preferred embodiment, device 41 further includes a sealing lip such as the one described with reference to pre-treatment tray 30 of FIG. 3. In alternative embodiments, device 41 is comprised of heatable plastics, which can be formed on the teeth and gums during placement. An adhesive or a repelling substance such as Vaseline™ may also be used to further ensure sealing.

Figure 5A:
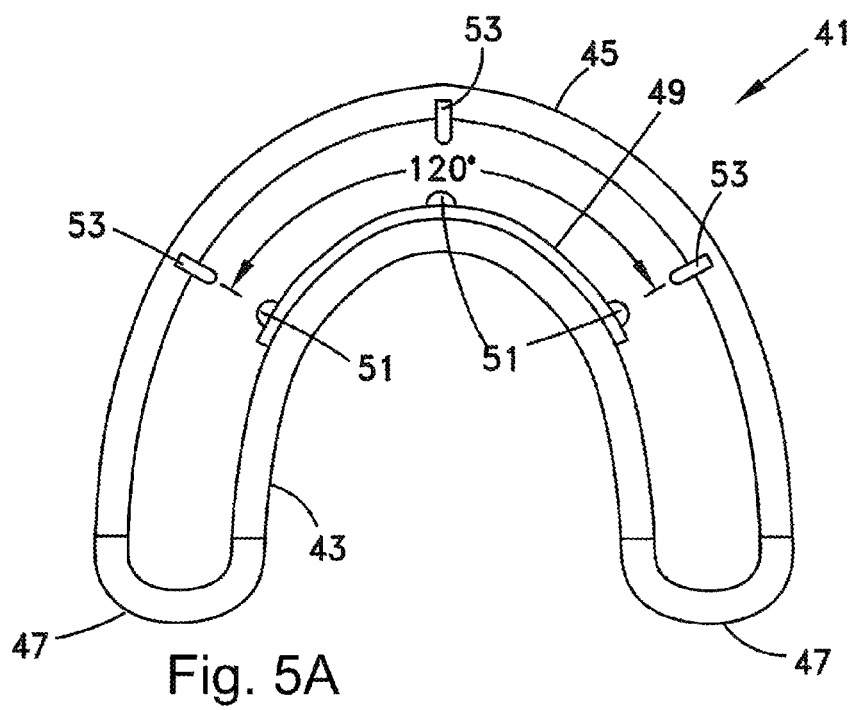
FIGS. 5a and 5b are cross-sectional illustrations of the electrochemical dental treatment device of FIG. 4, in accordance with a preferred embodiment of the present invention.
Figure 5B:
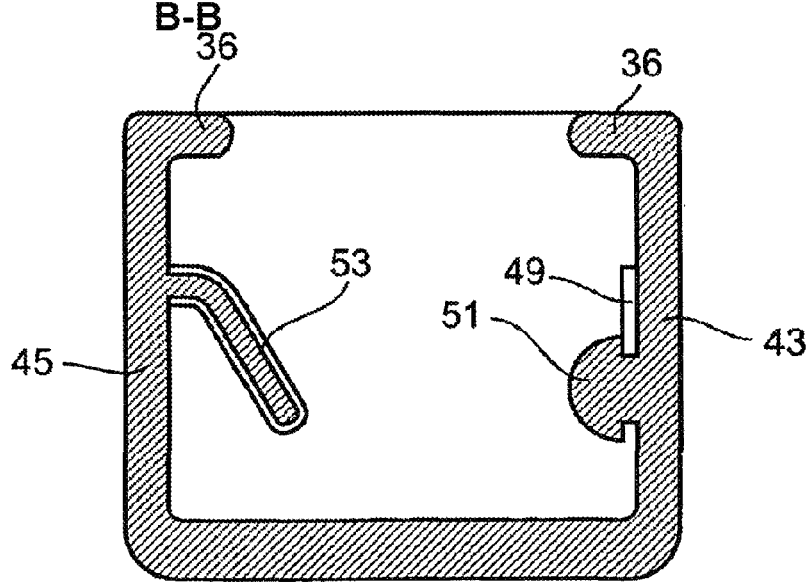

Reference is now made to FIGS. 5a and 5b, which are cross sectional illustrations of device 41 along lines A-A and B-B, respectively, illustrated in FIG. 4. As shown in FIG. 5a, spacers 51 may contact the back of the teeth, while contact electrodes 53 are designed to contact the front of the teeth. As shown in FIG. 5b, spacers 51 are fixed, and contact electrodes 53 are attached to front curved wall 45 by a spring-like mechanism, for providing spring-like nature and behavior to contact electrodes 53. In the exemplary embodiment shown in FIG. 5b, the spring-like nature and behavior are accomplished by placing contact electrode 53 at an angle, for example, of about 45 degrees. Alternatively, actual springs may used for providing spring-like nature and behavior to contact electrodes 53. In a preferred embodiment, three contact electrodes 53 contact three different teeth. The contact area of contact electrodes 53 is minimal, so as to induce current into the teeth, while avoiding occurrence of the competitive reaction of water electrolysis (i.e., electrolytic degradation of water).

Figure 6A:
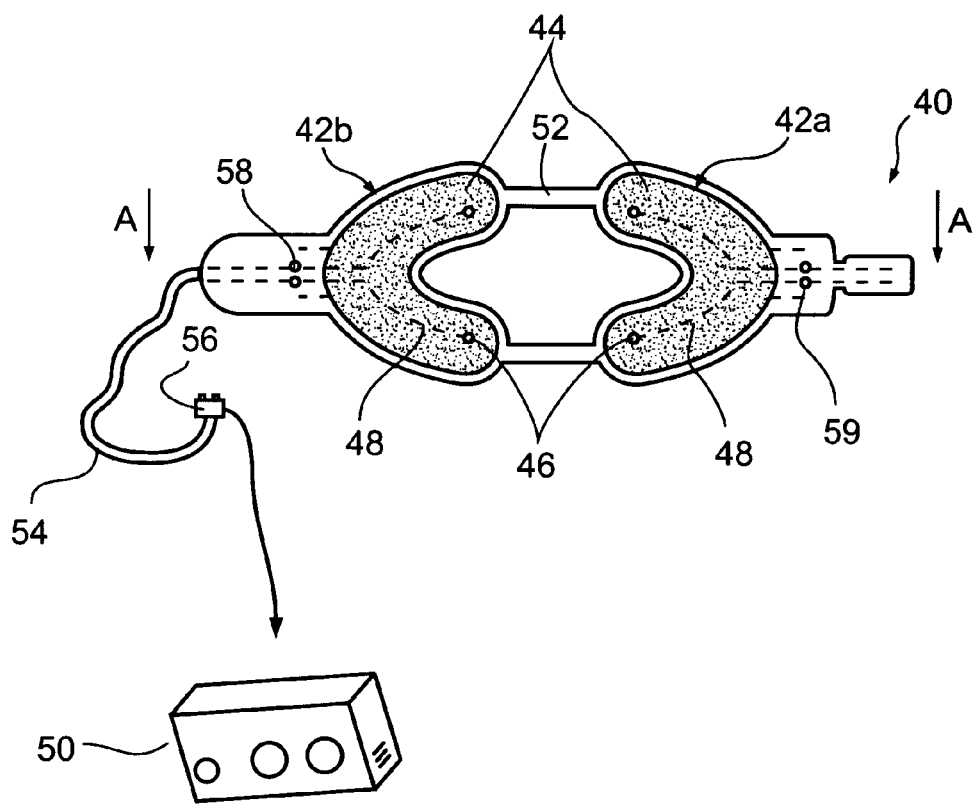
FIGS. 6a and 6b are diagrammatic and cross-sectional views of a device for electrochemically treating teeth, in accordance with another preferred embodiment of the present invention.
Figure 6B:
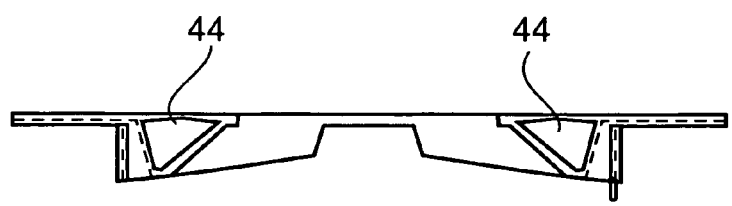
Figure 7A:
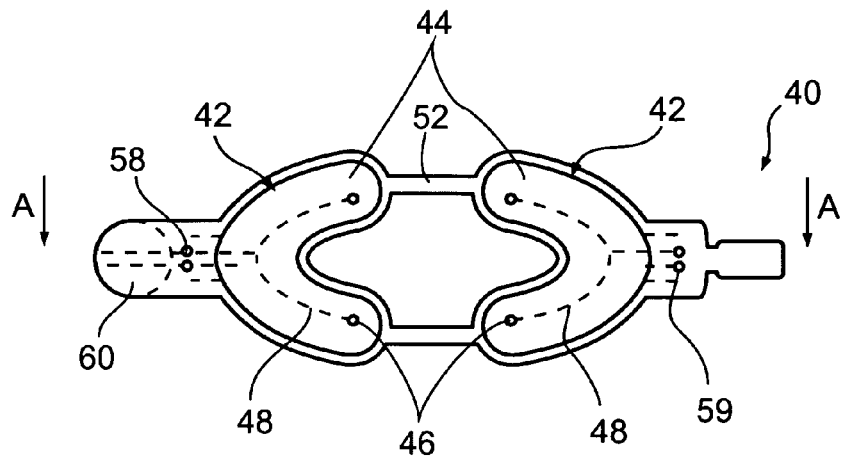
FIGS. 7a and 7b are diagrammatic and cross-sectional views of an electrochemical dental treatment device, in accordance with yet another preferred embodiment of the present invention.
Figure 7B:
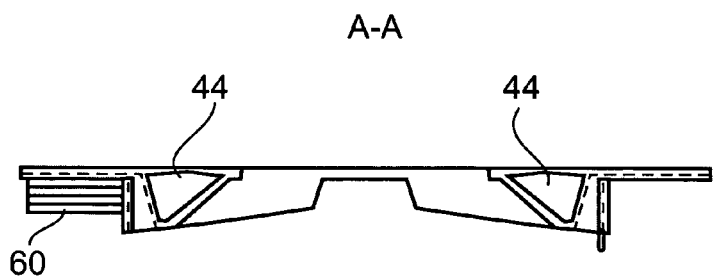

Reference is now made to FIGS. 6a and 6b, which are an illustration and a cross-sectional view, respectively, of an apparatus 40, for fluoride treatment, i.e., when the present invention is implemented particularly for fluorinating teeth, or, alternatively, for teeth whitening treatment, i.e., when the present invention is implemented particularly for whitening teeth, in accordance with another embodiment of the present invention. Apparatus 40 includes a set of trays 42, including an upper tray 42a and a lower tray 42b, each of which has wells 44 for holding an ionizable substance, for example, either being, or including, a fluoride solution or gel composition, for immersion of teeth therein, i.e., when the present invention is implemented particularly for fluorinating teeth, or, alternatively, for holding an oxidizing agent, for example, either being, or including, a form of hydrogen peroxide, such as a solution form of hydrogen peroxide, for immersion of teeth therein, i.e., when the present invention is implemented particularly for whitening teeth.

As shown in FIG. 6a, trays 42 have plugs and electrodes 46 positioned therein, which are connected via conducting wires 48 to a power supply 50. Electrodes are comprised of inert, electricity conducting, material, such as stainless steel, platinum, gold, or any other suitable electricity conducting metal. In a preferred embodiment, trays 42 are comprised of a non-conducting material, such as a biocompatible plastic material. It should be noted that any biocompatible plastic material which does not react with fluoride, i.e., when the present invention is implemented particularly for fluorinating teeth, or, alternatively, which does not react with an oxidizing agent, for example, hydrogen peroxide, i.e., when the present invention is implemented particularly for whitening teeth, may be used as material of construction of trays 42a and 42b.

Trays 42, and wells 44, are sized in accordance with standard sized dental trays. In one embodiment, the upper and the lower trays 42 are connected to each other via a folding bridge 52, which allows both trays 42 to be placed on the teeth simultaneously by folding the trays back in the area of folding bridge 52. An electrical connector 54 connects electrodes 48 to power source 50, via a plug 56, or via any other suitable means. Plug 56 is designed to fit into power source 50.

Furthermore, upper and lower trays 42 are connectable to one another via a socket 58 and a socket connector 59. Socket 58 is located on an outer rim of one of trays 42, for example, tray 42b, as shown in FIG. 6a, such that when trays 42 are folded at folding bridge 52, socket connector 59, located on an outer rim of the other tray, for example, tray 42a, as shown in FIG. 6a, connects the two trays 42 and completes the electrochemical circuit. In another embodiment, the trays 42 are not connected to each other.

In one embodiment, as shown in FIG. 6a, device 40 is connected to a regular power supply, with a standard AC/DC transformer. In another embodiment, rechargeable batteries (1-12 volt) are used. In yet another embodiment, shown in FIGS. 7a and 7b, a disposable battery 60 is embedded in device 40, allowing it to be more easily transportable.

It should be readily apparent, that in all of the herein illustratively described embodiments of the present invention, the electrochemical circuit runs through device 40, and not through any non-intra-oral cavity body part of the user. In this way, fluoride ionization can be increased, thus enhancing fluoride uptake by the teeth, i.e., when the present invention is implemented particularly for fluorinating teeth, or, alternatively, in this way, oxidizing activity by the oxidizing agent can be increased, thus, enhancing oxidizing agent uptake by the teeth, i.e., when the present invention is implemented particularly for whitening teeth.

In one embodiment, different sized pre-treatment trays 30 and devices 41 are provided for different sized individuals.

Figure 8:
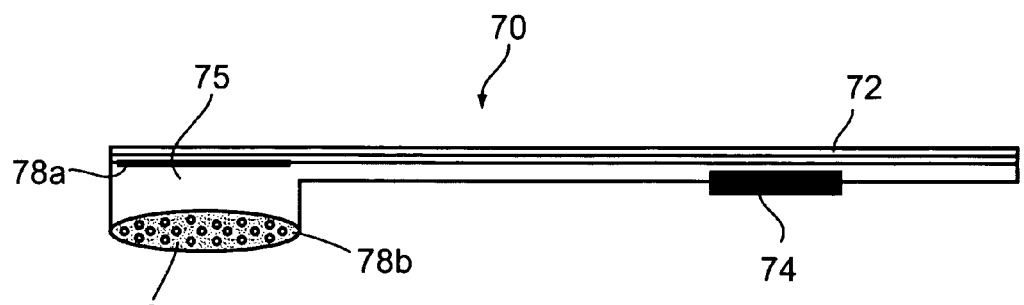
FIG. 8 is a view of an electrochemical toothbrush, in accordance with another preferred embodiment of the present invention.

Reference is now made to FIG. 8, which is an illustration of an electrochemical dental treatment toothbrush 70, in accordance with another embodiment of the present invention. Toothbrush 70 includes a handle 72 having a battery 74 placed therein, and a head portion 75 at an opposite end thereof. Head portion 75 includes a bristle portion 76 on a lower end thereof, and further has two electrodes 78—a cathode 78a on an upper end, and an anode 78b in an area of the bristles. An electrochemical circuit is completed through cathode 78a, the tooth which is in contact with bristle portion 76, and anode 78b. Toothbrush 70 can be used with an ionizable substance, for example, either being, or including, a fluoride gel or paste composition, for brushing teeth therein, i.e., when the present invention is implemented particularly for fluorinating teeth, as in the dental trays illustratively described hereinabove, to increase fluorination of the teeth. Alternatively, toothbrush 70 can be used to decrease the plaque on the tooth surface. Alternatively, toothbrush 70 can be used with an oxidizing agent, for example, either being, or including, a form of hydrogen peroxide, such as a gel or paste form of hydrogen peroxide, for brushing of teeth therein, i.e., when the present invention is implemented particularly for whitening teeth. The electrochemical circuit of the toothbrush 70 of the present invention does not run through a non-intra-oral cavity body part of an individual.

The fluoride gel is provided in the form of a compound, and is suitable for donating fluoride ions. Examples of such compounds include but are not limited to sodium fluoride, lithium fluoride, amino fluoride, tin fluoride, a combination of fluoride donor compounds, or any other suitable compound which is readily ionizable.

Figure 9:
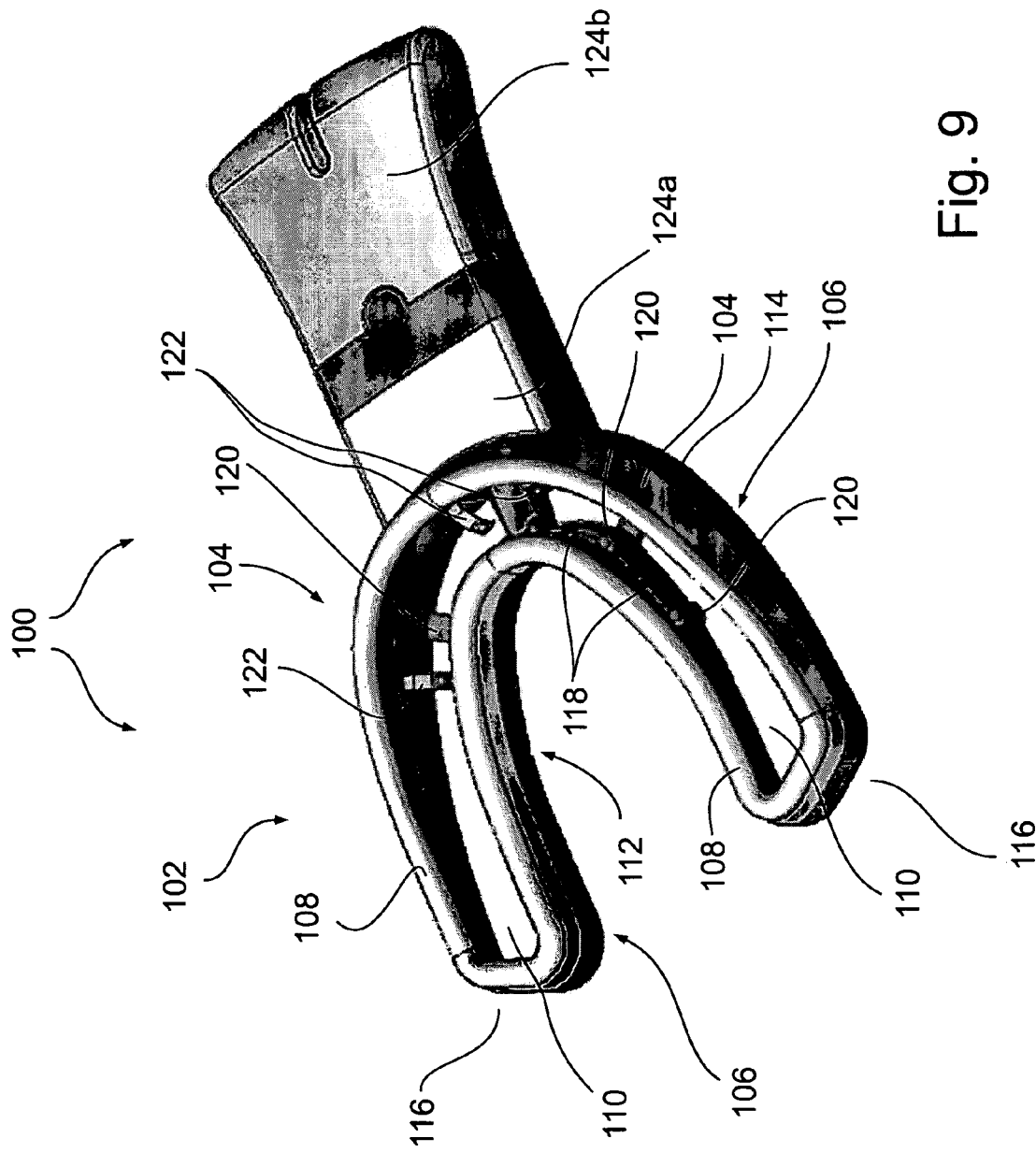
FIGS. 9 and 10 are schematic diagrams illustrating perspective views of another exemplary preferred embodiment of an electrochemical dental treatment device, for electrochemically treating teeth, showing the replaceable/rechargeable power supply in a connected or closed configuration (FIG. 9), and in a disconnected or open configuration (FIG. 10), in accordance with the present invention.
Figure 10:
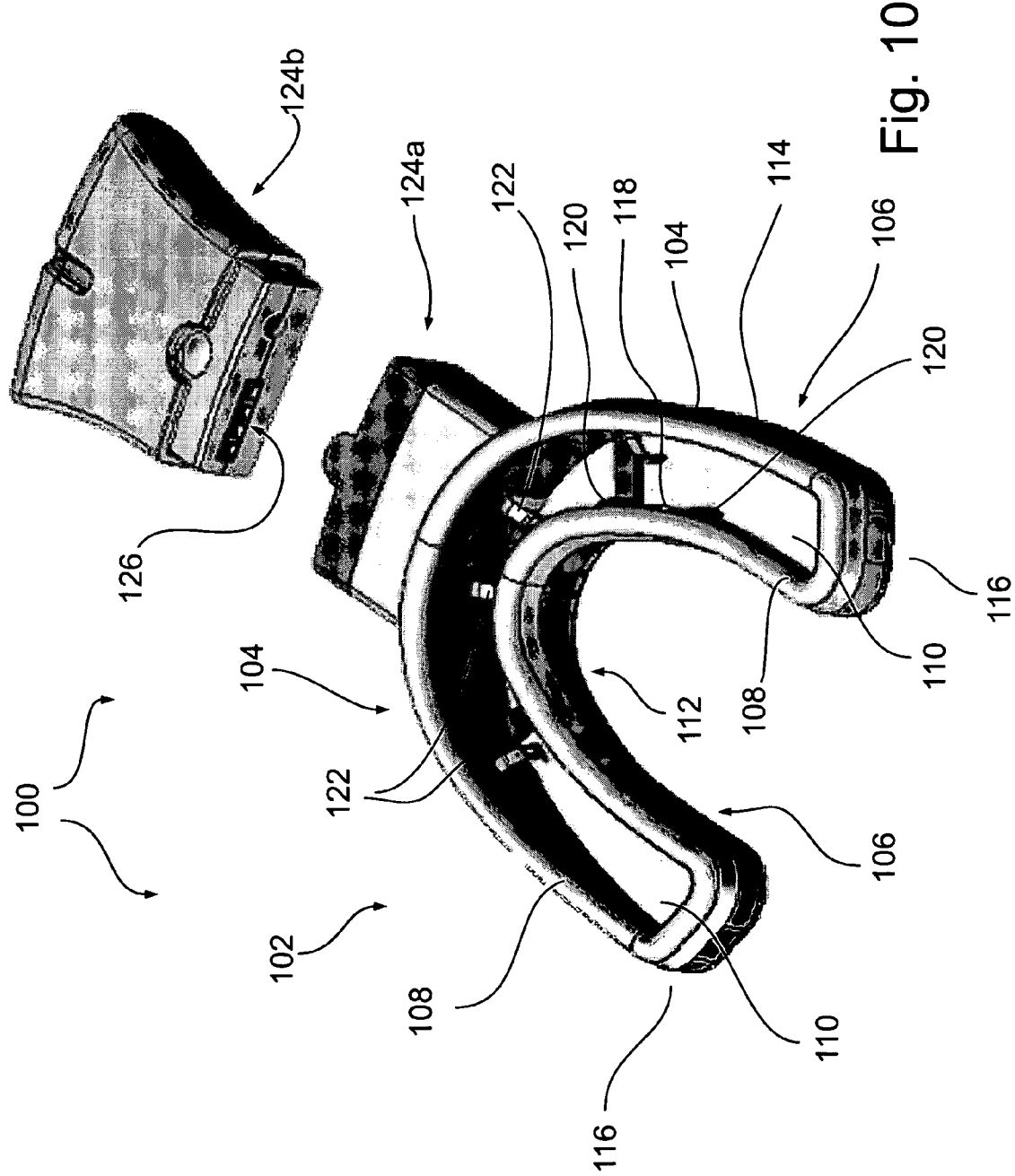

FIGS. 9 and 10 are schematic diagrams illustrating perspective views of another exemplary preferred embodiment of an electrochemical dental treatment device 100, for electrochemically treating teeth, showing the replaceable/rechargeable power supply in a connected or closed configuration (FIG. 9), and in a disconnected or open configuration (FIG. 10), in accordance with the present invention.

In FIGS. 9 and 10, electrochemical dental treatment device 100 is usable for electrochemical ion exchange fluoride treatment, i.e., when the present invention is implemented particularly for fluorinating teeth, or, alternatively, which is usable for electrochemical redox reactions involving the oxidizing agent, in teeth whitening treatment, i.e., when the present invention is implemented particularly for whitening teeth, in accordance with a preferred embodiment of the present invention. Device 100 includes a tray designed to hold an ionizable substance, for example, either being, or including, fluoride solution or gel composition, for immersion of teeth therein, i.e., when the present invention is implemented particularly for fluorinating teeth, or, alternatively, is designed to hold an oxidizing agent, for example, either being, or including, a form of hydrogen peroxide, such as a solution form of hydrogen peroxide, for immersion of teeth therein, i.e., when the present invention is implemented particularly for whitening teeth.

In electrochemical dental treatment device 100, treatment tray 102 has an upper portion 104 and a lower portion 106. Upper portion 104 preferably includes a sealing lip 108, such as the one described with reference to pre-treatment tray 30 of FIG. 3, which is designed to contact the gums, thus, sealing tray 102 onto the gums and substantially preventing leaking out of solution or gel compositions used during the electrochemical treatment of the teeth. Lower portion 106 includes a space 110, within which the teeth are appropriately positioned for performing the electrochemical treatment. In one embodiment of the present invention, tray 102 is comprised of a plastic material. Alternatively, an adhesive material which is biocompatible (such as, for example, beeswax) may be added to sealing lip 108 to ensure sealing of tray 102 onto the gums.

Electrochemical dental treatment device 100 is of a shape similar to typical dental trays, including a back curved wall 112 and a front curved wall 114 joined together at end sections 116. Back curved wall 112 includes an electrode 118, which is the negative electrode, or the anode. Electrode 118 is comprised of a thin, flexible metal strip attached to an inner portion of back curved wall 112. In a preferred embodiment, electrode 118 is comprised of stainless steel. In alternative embodiments, electrode 118 is comprised of any inert, electricity conducting, material, such as, platinum, gold, or any other suitable electricity conducting metal. Spacers 120 are positioned along electrode 118, and are designed to preclude contact between electrode 118 and teeth positioned within device 100, while providing contact between the ionizable substance, such as fluoride solution or gel composition, or, alternatively, the oxidizing agent, such as hydrogen peroxide solution, within device 100 and electrode 118. Spacers 120 are comprised of insulating materials, such as plastics.

Front curved wall 114 includes contact electrodes 122, which are positive electrodes, or cathodes, and are designed to be placed in direct contact with the front of teeth within device 100. Contact electrodes 122 are attached to front curved wall 114 by a spring-like mechanism, ensuring contact between contact electrodes 122 and the teeth. Preferably, at least three contact electrodes 122 are used, each one designed to contact a different tooth. The contact area between contact electrodes 122 and the teeth is minimized. In alternative embodiments, device 100 is comprised of heatable plastics, which can be formed on the teeth and gums during placement. An adhesive or a repelling substance such as Vaseline™ may also be used to further ensure sealing of treatment tray 102 onto the gums.

In an exemplary preferred embodiment, as shown in FIGS. 9 and 10, electrochemical dental treatment device 100 includes a mobile current supply unit 124b containing a disposable or rechargeable battery operative in a range of between about 0.001 volt and about 12 volts. Mobile current supply unit 124b is operatively (physically and electrically) connectable, via connector assembly 124a, to device 100. Preferably, connector assembly 124a is connected or attached to the central portion of front curved wall 114. Mobile current supply unit 124b is physically and electrically connectable, for example, via a female configured electrical contact assembly 126 (FIG. 10), to a male configured electrical contact or lead assembly (not shown) included as part of connector assembly 124a. Preferably, mobile current supply unit 124b includes a light window or indicator light, for example, as shown by the inserted section located at the outer end of mobile current supply unit 124b, for indicating a condition of 'power on', i.e., when mobile current supply unit 124b actively supplies current to electrochemical dental treatment device 100, thereby indicating that electrochemical dental treatment device 100 is in an 'on' mode for electrochemically treating teeth.

A main aspect of the present invention is provision of a method for treating a tooth, including the following main procedures, and, components and functionalities thereof: applying a metal salt solution to a tooth, applying an ionizable substance to the tooth, and applying a current flow to the tooth so as to ionize the ionizable substance.

Accordingly, the method of pre-treating teeth for fluoride uptake used in accordance with the apparatus described above is as follows, in accordance with one embodiment of the present invention. Initially, teeth are thoroughly cleaned, either by professional cleaning or using a regular toothbrush. Next, teeth are rinsed with distilled water.

A metal catalyst solution, which functions as an activating solution, is prepared by dissolving different amounts of metal, or metal salt, solutions, such as of silver, copper, titanium, or palladium, in an amount of distilled water such that the concentration of the metal is in a range of between about 0.01% and about 3% by weight. In alternative exemplary preferred embodiments, the metal, or metal salt, solution can include silver nitrate, palladium hydroxide, palladium chloride, or copper chloride, salts, or any other suitable activator. In one specific example, 100 mg of silver nitrate is dissolved in 10 ml distilled water. In yet another specific example, 50 mg of copper chloride is dissolved in 10 ml of distilled water. Pre-treatment tray 30 (FIG. 3) is placed on the teeth, preferably, in such a way that all of the teeth are in contact with absorbent material 38, for example, a sponge. Sealing lip 36 is placed in contact with the gums to seal tray 30 and prevent leaking of solution into the mouth. A pre-measured amount of the metal catalyst (activating) solution is then introduced into tray 30 by injection or any other filling procedure, such that full contact between the teeth and the solution is obtained, for a time period of approximately 1 minute. Alternatively, a known amount of metal catalyst (activating) solution is placed into pretreatment tray 30 prior to placing tray 30 in the mouth. After pretreatment, tray 30 is removed from the mouth, taking care to avoid spilling of the activating solution into the mouth. The teeth are then rinsed with distilled water again.

After pretreatment, fluoride treatment is commenced. A fluoride donor solution is prepared as follows. The following description of the preparation of the fluoride donor solution includes sodium fluoride, but it should be readily apparent that this is merely exemplary, and that the fluoride solution is not limited to this compound. Sodium fluoride solution in a range of 1-5% is prepared by dissolving an appropriate amount of sodium fluoride salt in distilled water. Sodium fluoride solution is incorporated into a gel, such as alginate and added to an apparatus of the present invention, either by filling the trays of the dental tray embodiment, or by coating the bristles of a toothbrush such as the one described above. In a preferred embodiment, a commercial fluoride gel having a 2.5% concentration is combined with 0.5 grams of sodium chloride (used as electrolyte) dissolved in 25 ml of distilled water, providing a total percentage of fluoride ions as 1.25%. In an alternative embodiment, 25 grams of Elmex™ Gel is mixed with a solution of 0.7 grams of sodium fluoride, followed by combination with 0.5 grams of sodium chloride and dissolution in 25 ml of distilled water. A power supply of 0-12 volts is used. The electrochemical circuit is then activated with a voltage in a range of between about 0.001 volt and about 12 volts. In a preferred embodiment, the voltage is in a range of between about 3 volts to about 9 volts, and most preferably is approximately 6 volts. The electrochemical circuit remains open for a predetermined period of time, in the range of between about 5 minutes and about 20 minutes. The current does not exceed about 30 milliamps (mA).

In one embodiment, a kit is provided, wherein a suitable sized pre-treatment tray 30, a suitable sized device 41, and a compatible amount of pre-measured activation solution and fluoride donor solution are provided. Different kits may be provided for different sized and aged individuals.

Another main aspect of the present invention is provision of a method for electrochemically whitening a tooth, including the following main procedures, and, components and functionalities thereof: applying a metal salt solution to a tooth, applying an oxidizing agent to the tooth, and applying a current flow to the tooth so as to activate and reduce the oxidizing agent for effecting whitening of the tooth.

Accordingly, the method of pre-treating teeth for enhanced teeth whitening used in accordance with the apparatus described above is as follows, in accordance with one embodiment of the present invention. Initially, teeth are thoroughly cleaned, either by professional cleaning or using a regular toothbrush. Next, teeth are rinsed with distilled water.

A metal catalyst solution, which functions as an activating solution, is prepared by dissolving different amounts of metal, or metal salt, solutions, such as of silver, copper, titanium, or palladium, in an amount of distilled water such that the concentration of the metal is in a range of between about 0.01% and about 3% by weight. In alternative exemplary preferred embodiments, the metal, or metal salt, solution can include silver nitrate, palladium hydroxide, palladium chloride, or copper chloride, salts, or any other suitable activator. In one specific example, 100 mg of silver nitrate is dissolved in 10 ml distilled water. In yet another specific example, 50 mg of copper chloride is dissolved in 10 ml of distilled water. Pre-treatment tray 30 (FIG. 3) is placed on the teeth, preferably, in such a way that all of the teeth are in contact with absorbent material 38, for example, a sponge. Sealing lip 36 is placed in contact with the gums to seal tray 30 and prevent leaking of solution into the mouth. A pre-measured amount of the metal catalyst (activating) solution is then introduced into tray 30 by injection or any other filling procedure, such that full contact between the teeth and the solution is obtained, for a time period of approximately 1 minute. Alternatively, a known amount of metal catalyst (activating) solution is placed into pre-treatment tray 30 prior to placing tray 30 in the mouth. After pretreatment, tray 30 is removed from the mouth, taking care to avoid spilling of the activating solution into the mouth. The teeth are then rinsed with distilled water again.

After pre-treatment of the teeth, whitening treatment is commenced. An oxidizing agent, for example, a tooth whitening agent, such as a commercial tooth whitening gel or solution, including hydrogen peroxide, or any other suitable oxidizing agent (e.g., ion, free radical donor) is placed in the tray of any one of the above illustratively described embodiments of the electrochemical dental treatment device, and then the tray is placed on the teeth in such a manner that all of the teeth are in contact with the oxidizing agent (whitening agent). The electrochemical circuit of the electrochemical dental treatment device is then activated, via a power supply, using a voltage in a range of between about 0.001 volt and about 12 volts. In a preferred embodiment, the voltage is in a range of between about 3 volts and about 9 volts, and most preferably, is approximately 6 volts. The electrochemical circuit remains open for a predetermined period of time, for example, in a range of between about 3 minutes and about 20 minutes. Preferably, the current passing through the electrochemical circuit does not exceed about 30 milliamps (mA).

Additional objects, advantages, and novel features of the present invention will become apparent to one ordinarily skilled in the art upon examination of the following example, which is not intended to be limiting. Additionally, each of the various embodiments and aspects of the present invention as delineated hereinabove and as claimed in the claims section below finds experimental support in the following example.

EXAMPLE

Reference is now made to the following example, which together with the above description, illustrate the invention in a non-limiting fashion.

Example

Electrochemically Treating (Fluorinating) Teeth

This is an example of implementing the hereinabove illustratively described invention of electrochemically treating teeth, particularly for fluorinating teeth.

Experimental Procedure

Fresh extracted teeth were washed with hydrogen peroxide solution (18%) for decontamination prior to use. Teeth were split into five groups, as follows:

Group A (control, n=3): No pretreatment, No gel treatment.

Group B (n=3): No pretreatment, Teeth immersed for 10 minutes in prepared fluoride gel, no current.

Group C (n=3): Yes pretreatment (immersed in 1% silver nitrate solution for 1 minute), Teeth immersed for 10 minutes in prepared fluoride gel, no current.

Group D (n–3): No pretreatment, Teeth immersed for 10 minutes in prepared fluoride gel with electric current.

Group E (n=3): Yes pretreatment (immersed in 1% silver nitrate solution for 1 minute), Teeth immersed for 10 minutes in prepared fluoride gel with electric current.

All teeth were then rinsed with water and placed in 5% lactic acid solution, having a pH of 1.9, and left in lactic acid solution for different time periods, ranging from 15 to 4500 minutes. At each time period, the tooth was rinsed with distilled water and tested by scratching with a sharp metal tool. If the scratching resulted in a scratch mark, the tooth was considered to have failed the test. If no scratch mark resulted, the tooth was considered to have passed the test.

Experimental Results

Figure 11:
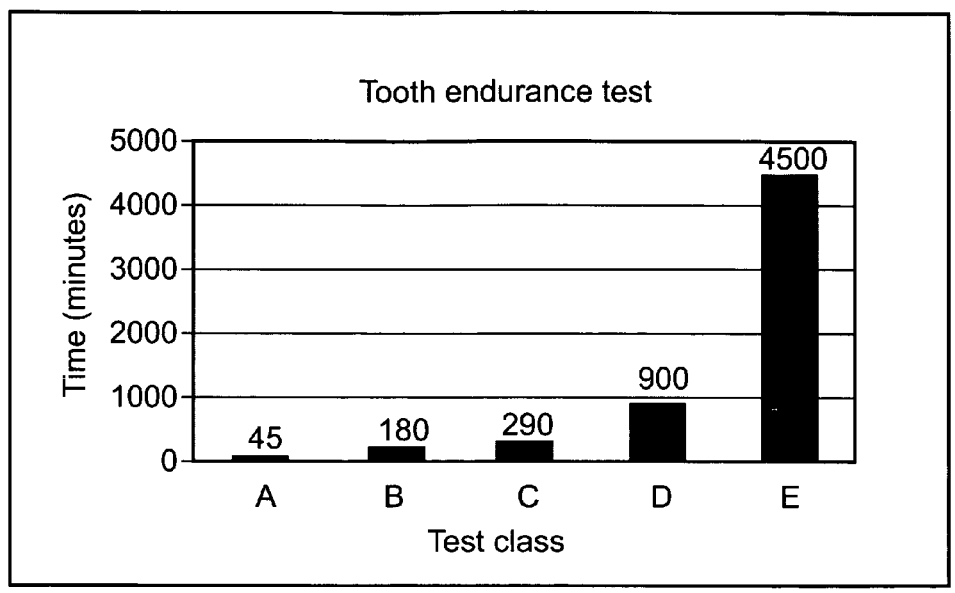
FIG. 11 is a bar graph illustration of results of using the method for treating a tooth, especially applicable for fluorinating a tooth, in accordance with a preferred embodiment of the present invention.

Results for the above experiment are summarized in FIG. 11, in bar graph format.

To summarize, the teeth from Group A (control) failed after an average of 45 minutes of exposure. Teeth from Group II failed after 2-3 hours of exposure. Teeth from Group III failed after 4-5 hours of exposure. Teeth from Group IV failed after approximately 15 hours of exposure. Teeth from Group V lasted at least 75 hours.

The above results show that teeth with pretreatment and current are significantly stronger than all other combinations.

Based on the above results, it is clear that pretreatment of teeth with a metal or metal salt solution, followed by connection to a circuit in an electrolyte having fluoride or a fluoride releasing substance, enhances and accelerates fluorination of the teeth, which results in increased physical resistance of the teeth against decay. This procedure can be accomplished with either an electrochemical dental device or an electrochemical toothbrush, as illustratively described hereinabove. The treatment is relatively short, and low in cost. It may be performed by any clinician, such as a dentist or hygienist, or by oneself.

As an alternative to the exemplary fluorination process described above, the present invention can be implemented for whitening teeth, using the hereinabove proposed method and device.

The present invention, as illustratively described and exemplified hereinabove, has several beneficial and advantageous aspects, characteristics, and features, which are based on or/and a consequence of, the above illustratively described main aspects of novelty and inventiveness.

First, for fluorinating teeth, implementation of the present invention provides excellent control of (electrochemically) applying, delivering, or dispensing, of fluoride to teeth, and involves minimal exposure of non-intra-oral cavity body parts to fluoride.

Second, for whitening teeth, implementation of the present invention provides excellent control of (electrochemically) applying, delivering, or dispensing, of teeth whitening oxidizing agents to teeth, and involves minimal exposure of non-tooth intra-oral cavity components, e.g., gum and tissue exterior surfaces, to oxidizing agents.

Third, the present invention is relatively simple and inexpensive to manufacture, and is relatively simple, safe, and inexpensive, to implement either by a dental health provider in a dental health office, or by oneself outside of a dental health office, and is commercially applicable.

Accordingly, based upon the above indicated aspects of novelty and inventiveness, and, beneficial and advantageous aspects, characteristics, and features, the present invention successfully addresses and overcomes shortcomings and limitations, and widens the scope, of presently known techniques for treating (fluorinating, or whitening) teeth.

It is appreciated that certain aspects and characteristics of the invention, which are, for clarity, described in the context of separate embodiments, may also be provided in combination in a single embodiment. Conversely, various aspects and characteristics of the invention, which are, for brevity, described in the context of a single embodiment, may also be provided separately or in any suitable sub-combination.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the scope of the appended claims.

What is claimed is:

1. A kit for dental treatment, the kit comprising an electrochemical device, a substance, and an activating solution:
   a) said device comprising an applicator for applying a substance to a tooth, said applicator forming a dental tray having a back curved wall and a front curved wall, defining therebetween a teeth receiving channel;
      a spacer connected to said back curved wall of said applicator;
      a first electrode attached to said back curved wall of said applicator, said first electrode connected to said spacer to preclude a contact of said first electrode with teeth;
      a second electrode attached to said front curved wall of said applicator, said second electrode being extending from said front curved wall so that said electrode would be in direct contact with teeth when said applicator is worn;

a sealing lip connected to said back curved wall and said front curved wall, operative to substantially prevent leaking out of substance or activation solution;

wherein said first electrode and said second electrode are configured to produce a current flow through said applicator but not through a non-intra-oral cavity body part, both electrodes being positioned inside said tray; and wherein said sealing lip minimizes exposure of non-intra-oral cavity body parts to said substance;

b) said substance being an ionizable substance placed within said applicator and undergoing ionization upon application of said current flow, wherein the tooth surface absorbs the ionizable substance, said absorption improved by first applying said activating solution to the tooth;

c) said activating solution being a metal salt solution which may be applied to a tooth before said ionization to enhance the absorption of said ionizable substance.

2. The kit of claim 1, wherein said ionizable substance is a fluoride donor compound.

3. The kit of claim 2, wherein said fluoride donor compound is enriched with sodium fluoride, lithium fluoride, amino fluoride, tin fluoride, or a combination of fluoride donor compounds.

4. The kit of claim 1, wherein said first electrode is a negative electrode.

5. The kit of claim 4, wherein said first electrode is a flat metal strip.

6. The kit of claim 5, wherein said spacers are comprised of a biocompatible plastic material.

7. The kit of claim 1, wherein said second electrode is a positive electrode.

8. The kit of claim 7, wherein said second electrode further comprises a spring mechanism.

9. The kit of claim 7, wherein said second electrode includes three electrode members, and wherein each of said three electrode members is configured to contact a different tooth at a contact area on each tooth.

10. The kit of claim 9, wherein said contact area is minimized.

11. The kit of claim 1, further comprising a power supply.

12. The kit of claim 11, wherein said power supply is an external power supply.

13. The kit of claim 11, wherein said power supply is a rechargeable battery.

14. The kit of claim 11, wherein said power supply is a disposable battery embedded within said applicator.

15. The kit of claim 1, wherein said metal salt solution is selected from the group consisting of silver nitrate, palladium hydroxide, palladium chloride, and copper chloride.

16. A kit for whitening a tooth, the kit comprising an electrochemical device, a substance, and an activating solution:

a) said device comprising an applicator for applying a substance to a tooth, said applicator forming a dental tray having a back curved wall and front curved wall, defining therebetween a teeth receiving channel;

a spacer connected to said back curved wall of said applicator;

a first electrode attached to said back curved wall, said first electrode connected to said spacer to preclude a contact of said first electrode with teeth;

a second electrode attached to said front curved wall, said second electrode extending from said front curved wall so that said electrode would be in direct contact with teeth when said applicator is worn;

a sealing lip connected to said back curved wall and said front curved wall, operative to substantially prevent leaking out of substance or activation solution;

wherein said first electrode and said second electrode are configured to produce a current flow through said applicator but not through a non-intra-oral cavity body part; and wherein said sealing lip minimizes exposure of non-intra-oral cavity body parts to said substance;

b) said substance being an oxidizing agent placed within said applicator and undergoing activation and reduction upon application of said current flow, wherein the tooth surface absorbs the substance, thereby effecting the whitening of the teeth, said absorption improved by first applying said activating solution to the tooth;

c) said activating solution being a metal salt solution which may be applied to a tooth before said activation and reduction to enhance said absorption of the substance.

17. The kit of claim 16, wherein said oxidizing agent is a tooth whitening agent.

18. The device of claim 17, wherein said tooth whitening includes hydrogen peroxide.

19. The kit of claim 16, wherein said first electrode is a positive electrode.

20. The kit of claim 19, wherein said first electrode is a flat metal strip.

21. The kit of claim 20, wherein said spacers are comprised of a biocompatible plastic material.

22. The kit of claim 16, wherein said second electrode is a negative electrode.

23. The kit of claim 22, wherein said second electrode further comprises a spring mechanism.

24. The kit of claim 22, wherein said second electrode includes three electrode members, and wherein each of said three electrode members is configured to contact a different tooth at a contact area on each tooth.

25. The kit of claim 24, wherein said contact area is minimized.

26. The kit of claim 16, further comprising a power supply.

27. The kit of claim 26, wherein said power supply is an external power source.

28. The kit of claim 26, wherein said power supply is a rechargeable battery.

29. The kit of claim 26, wherein said power supply is a disposable battery embedded within said applicator.

30. The kit of claim 16, wherein said metal salt solution is selected from the group consisting of silver nitrate, palladium hydroxide, palladium chloride, and copper chloride.

31. A device for dental treatment, the device comprising:

an applicator for applying a substance to a tooth which has been brought to contact with a metal salt activating solution, said applicator forming a dental tray having a back curved wall and a front curved wall, defining therebetween a teeth receiving channel;

a spacer connected to said back curved wall of said applicator;

a first electrode attached to said back curved wall of said applicator, said first electrode connected to said spacer to preclude a contact of said first electrode with teeth;

a second electrode attached to said front curved wall of said applicator, said second electrode extending from said front curved wall so that said electrode would be in direct contact with teeth when said applicator is worn;

a sealing lip connected to said back curved wall and said front curved wall;

wherein said first electrode and said second electrode are configured to produce a current flow through said applicator but not through a non-intra-oral cavity body part, both electrodes being positioned inside said tray; and wherein said sealing lip minimizes leaking out of said substance, and exposure of non-intra-oral cavity body parts to said substance;

said substance being an ionizable substance placed within said applicator and undergoing ionization upon application of said current flow, wherein the tooth surface absorbs the ionizable substance, said absorption improved by first applying said activating solution to the tooth.

32. A device for whitening a tooth, the device comprising:

an applicator for applying a substance to a tooth which has been brought to contact with a metal salt activating solution, said applicator forming a dental tray having a back curved wall and front curved wall, defining therebetween a teeth receiving channel;

a spacer connected to said back curved wall of said applicator;

a first electrode attached to said back curved wall, said first electrode connected to said spacer to preclude a contact of said first electrode with teeth;

a second electrode attached to said front curved wall, said second electrode extending from said second curved wall so that said electrode would be in direct contact with teeth when said applicator is worn;

a sealing lip connected to said back curved wall and said front curved wall;

wherein said first electrode and said second electrode are configured to produce a current flow through said applicator but not through a non-intra-oral cavity body part, both electrodes being positioned inside said tray; and wherein said sealing lip minimizes leaking out of said substance, and exposure of non-intra-oral cavity body parts to said substance;

said substance being an oxidizing agent placed within said applicator and undergoing activation and reduction upon application of said current flow, thereby effecting the whitening of the teeth, wherein the tooth surface absorbs the substance, said absorption improved by first applying said activating solution to the tooth.

* * * * *